(12) United States Patent
Wei et al.

(10) Patent No.: US 7,202,218 B2
(45) Date of Patent: Apr. 10, 2007

(54) OLIGOPEPTIDE ANTAGONIST OF INTERLEUKIN-6

(75) Inventors: Lin-Hung Wei, Taipei (TW); Jen-Liang Su, Taipei (TW); Min-Liang Kuo, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 11/195,674

(22) Filed: Aug. 3, 2005

(65) Prior Publication Data

US 2007/0032432 A1    Feb. 8, 2007

(51) Int. Cl.
*A61K 38/00* (2006.01)
(52) U.S. Cl. .......................................... 514/16; 530/300
(58) Field of Classification Search ................... None
See application file for complete search history.

(56) References Cited

U.S. PATENT DOCUMENTS

2004/0123343 A1*  6/2004  La Rosa et al. ............. 800/278

OTHER PUBLICATIONS

Su et al., "A Novel Peptide Specifically Binding to Interleukin-6 Receptor (gp80) Inhibits Angiogenesis and Tumor Growth", Cancer Res, vol. 65, pp. 4827-4835, Jun. 1, 2005.*
Salanoubat M. et al. "Genome Sequence of the Plant Pathogen Ralstonia solanacearum" 2002, Nature, vol. 415, pp. 497-502.*
Clinical Cancer Research, vol. 9, Oct. 15, 2003, pp. 4653-4665, Trikha et al.

* cited by examiner

*Primary Examiner*—B. Dell Chism
*Assistant Examiner*—Hemant Khanna
(74) *Attorney, Agent, or Firm*—Birch, Stewart, Kolasch & Birch, LLP (57) ABSTRACT

The present invention provides an antagonist peptide of interleukin-6 (IL-6), wherein the peptide comprises a amino acid sequence which is selected from the group consisting of SEQ ID NO: 5, SEQ ID NO: 6 and SEQ ID NO: 7. The peptide of the invention is able to specifically bind IL-6R and compete for the binding of IL-6 to IL-6R, to block IL-6-induced signal transduction and therefore effectively inhibits IL-6-mediated antiapotopsis and angiogenesis, and further inhibits IL-6-mediated tumor growth.

9 Claims, 9 Drawing Sheets

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial
<220> FEATURE:
<223> OTHER INFORMATION: A OLIGOPEPTIDE NONANTAGONIST OF INTERLEUKIN-6
<300> PUBLICATION INFORMATION:
<301> AUTHORS: Lin-Hung Wei, Jen-Liang Su and Min-Liang Kuo
<302> TITLE: A Novel Peptide Specifically Binding to Interleukin-6
      Receptor (gp80) Inhibits Angiogenesis and Tumor Growth
```

-continued

```
<303> JOURNAL: Cancer Research
<304> VOLUME: 65
<305> ISSUE: 11
<306> PAGES: 4827-4835
<307> DATE: 2005-06-01

<400> SEQUENCE: 1

Leu Ser Leu Met Pro Arg Leu
1               5

<210> SEQ ID NO 2
<211> LENGTH: 7
<212> TYPE: PRT
<213> ORGANISM: Artificial
<220> FEATURE:
<223> OTHER INFORMATION: A OLIGOPEPTIDE NONANTAGONIST OF INTERLEUKIN-6
<300> PUBLICATION INFORMATION:
<301> AUTHORS: Jen-Liang Su, Kuo-Pao Lai, Chi-An Chen, Ching-Yao Yang,
      Pei-Sheng Chen, Chiao-Chia Chang, Chia-Hung Chou, Chi-Lun Hu,
      Min-Liang Kuo, Chang-Yao Hsieh, and Lin-Hung Wei
<302> TITLE: A Novel Peptide Specifically Binding to Interleukin-6
      Receptor (gp80) Inhibits Angiogenesis and Tumor Growth
<303> JOURNAL: Cancer Research
<304> VOLUME: 65
<305> ISSUE: 11
<306> PAGES: 4827-4835
<307> DATE: 2005-06-01

<400> SEQUENCE: 2

Asn Pro Met Met Arg Pro Leu
1               5

<210> SEQ ID NO 3
<211> LENGTH: 7
<212> TYPE: PRT
<213> ORGANISM: Artificial
<220> FEATURE:
<223> OTHER INFORMATION: A OLIGOPEPTIDE NONANTAGONIST OF INTERLEUKIN-6
<300> PUBLICATION INFORMATION:
<301> AUTHORS: Jen-Liang Su, Kuo-Pao Lai, Chi-An Chen, Ching-Yao Yang,
      Pei-Sheng Chen, Chiao-Chia Chang, Chia-Hung Chou, Chi-Lun Hu,
      Min-Liang Kuo, Chang-Yao Hsieh, and Lin-Hung Wei
<302> TITLE: A Novel Peptide Specifically Binding to Interleukin-6
      Receptor (gp80) Inhibits Angiogenesis and Tumor Growth
<303> JOURNAL: Cancer Research
<304> VOLUME: 65
<305> ISSUE: 11
<306> PAGES: 4827-4835
<307> DATE: 2005-06-01

<400> SEQUENCE: 3

Gln Met Arg Thr Thr Ile Arg
1               5

<210> SEQ ID NO 4
<211> LENGTH: 7
<212> TYPE: PRT
<213> ORGANISM: Artificial
<220> FEATURE:
<223> OTHER INFORMATION: A OLIGOPEPTIDE NONANTAGONIST OF INTERLEUKIN-6
<300> PUBLICATION INFORMATION:
<301> AUTHORS: Jen-Liang Su, Kuo-Pao Lai, Chi-An Chen, Ching-Yao Yang,
      Pei-Sheng Chen, Chiao-Chia Chang, Chia-Hung Chou, Chi-Lun Hu,
      Min-Liang Kuo, Chang-Yao Hsieh, and Lin-Hung Wei
<302> TITLE: A Novel Peptide Specifically Binding to Interleukin-6
      Receptor (gp80) Inhibits Angiogenesis and Tumor Growth
<303> JOURNAL: Cancer Research
<304> VOLUME: 65
<305> ISSUE: 11
<306> PAGES: 4827-4835
<307> DATE: 2005-06-01

<400> SEQUENCE: 4
```

Arg Leu Met Met Leu Gln Gln
1               5

<210> SEQ ID NO 5
<211> LENGTH: 7
<212> TYPE: PRT
<213> ORGANISM: Artificial
<220> FEATURE:
<223> OTHER INFORMATION: A OLIGOPEPTIDE ANTAGONIST OF INTERLEUKIN-6
<300> PUBLICATION INFORMATION:
<301> AUTHORS: Jen-Liang Su, Kuo-Pao Lai, Chi-An Chen, Ching-Yao Yang,
      Pei-Sheng Chen, Chiao-Chia Chang, Chia-Hung Chou, Chi-Lun Hu,
      Min-Liang Kuo, Chang-Yao Hsieh, and Lin-Hung Wei
<302> TITLE: A Novel Peptide Specifically Binding to Interleukin-6
      Receptor (gp80) Inhibits Angiogenesis and Tumor Growth
<303> JOURNAL: Cancer Research
<304> VOLUME: 65
<305> ISSUE: 11
<306> PAGES: 4827-4835
<307> DATE: 2005-06-01

<400> SEQUENCE: 5

Met Leu Leu Gln Asn Arg Gln
1               5

<210> SEQ ID NO 6
<211> LENGTH: 7
<212> TYPE: PRT
<213> ORGANISM: Artificial
<220> FEATURE:
<223> OTHER INFORMATION: A OLIGOPEPTIDE ANTAGONIST OF INTERLEUKIN-6
<300> PUBLICATION INFORMATION:
<301> AUTHORS: Jen-Liang Su, Kuo-Pao Lai, Chi-An Chen, Ching-Yao Yang,
      Pei-Sheng Chen, Chiao-Chia Chang, Chia-Hung Chou, Chi-Lun Hu,
      Min-Liang Kuo, Chang-Yao Hsieh, and Lin-Hung Wei
<302> TITLE: A Novel Peptide Specifically Binding to Interleukin-6
      Receptor (gp80) Inhibits Angiogenesis and Tumor Growth
<303> JOURNAL: Cancer Research
<304> VOLUME: 65
<305> ISSUE: 11
<306> PAGES: 4827-4835
<307> DATE: 2005-06-01

<400> SEQUENCE: 6

Thr Leu Gln Ala Ser Ile Leu
1               5

<210> SEQ ID NO 7
<211> LENGTH: 7
<212> TYPE: PRT
<213> ORGANISM: Artificial
<220> FEATURE:
<223> OTHER INFORMATION: A OLIGOPEPTIDE ANTAGONIST OF INTERLEUKIN-6
<300> PUBLICATION INFORMATION:
<301> AUTHORS: Jen-Liang Su, Kuo-Pao Lai, Chi-An Chen, Ching-Yao Yang,
      Pei-Sheng Chen, Chiao-Chia Chang, Chia-Hung Chou, Chi-Lun Hu,
      Min-Liang Kuo, Chang-Yao Hsieh, and Lin-Hung Wei
<302> TITLE: A Novel Peptide Specifically Binding to Interleukin-6
      Receptor (gp80) Inhibits Angiogenesis and Tumor Growth
<303> JOURNAL: Cancer Research
<304> VOLUME: 65
<305> ISSUE: 11
<306> PAGES: 4827-4835
<307> DATE: 2005-06-01

<400> SEQUENCE: 7

Leu Ser Leu Ile Thr Arg Leu
1               5

OLIGOPEPTIDE ANTAGONIST OF INTERLEUKIN-6

BACKGROUND OF THE INVENTION

1. Field of the Invention

The present invention relates to an antagonist peptide of interleukin-6 (IL-6), which is able to specifically compete for the binding of IL-6 to its receptor and inhibits IL-6-mediated tumor growth.

2. The Prior Arts

Interleukin-6 is a pleiotropic secreted cytokine with a molecular weight of 22–27 kDa. The physiological activities of IL-6 are known to be mediated through binding to a membrane-bound glycoprotein IL-6 receptor (IL-6R) α chain protein (gp80) on target cells to process regulation. The IL-6/IL-6R complex, formed after the binding of IL-6 and IL-6R, activates the 1-chain protein of IL-6R (abbreviated hereafter as gp130) to express many biological functions. The IL-6/IL-6R complex initiates dimerization of gp130 from monomers, activates a cytoplasmic tyrosine kinase bound to gp130 of target cells, and then triggers 3 main signaling pathways, including Janus-activated kinase/signal transducers and activators of transcription (Jak/STAT), Ras/mitogen-activated protein kinase (MAPK) and phosphatidylinositol 3-kinase (PI3-K)/Akt signaling.

In addition, gp80 may be cleaved from the cellular membrane molecule by a transmembrane metalloproteinase or translated from an alternatively spliced mRNA to form a soluble receptor (sIL-6R). This soluble receptor binds IL-6 with an affinity similar to that of the receptor on the cellular membrane. And more importantly, the sIL-6R/IL-6 complex is capable of activating cells via interaction with membrane-bound gp130 to initiate the abovementioned signaling pathways. This unique feature makes the sIL-6R/IL-6 complex an agonist rather than an antagonist for target cells. On the other hand, elevated sIL-6R levels have been proved in numerous clinical conditions, indicating that the production of sIL-6R is part of the process in many diseases.

Through binding to gp130, IL-6 triggers various signal transductions, results in many different biological functions such as regulating inflammation, immuno-responses, hepatic acute-phase protein synthesis, and other important physiological functions. Most importantly, IL-6 signaling mediated via gp130 has been proved to interfere with many cellular functions, such as cell apoptosis, cell differentiation, cell migration and tumor angiogenesis, etc. And it is also critically implicated in the pathogenesis of various human cancers, including multiple myeloma, Kaposi's sarcoma, prostate cancer and cervical cancer.

As mentioned above, IL-6 plays a pivotal role in many disease processes. With the progress in molecular biology and the understanding in IL-6, IL-6R and their signaling pathways, using IL-6R as a molecular target shows great potential in the clinical applications. Therefore, Trikha M. et al. have suggested (Clin. Cancer Res. 2003; 9: 4653–4665) the feasibility of targeting-IL-6R cancer therapy, which used anti-IL-6 monoclonal antibodies to block IL-6 dependent processes. However, because of the complicated ways of preparation and high production cost of monoclonal antibodies, people who skilled in the art will understand that the use of monoclonal antibodies is limited in industrial application.

SUMMARY OF THE INVENTION

To solve the abovementioned problems of the known technology, a primary object of the present invention is to provide an oligopeptide which could specifically recognize and bind the IL-6R to block the binding of IL-6 and IL-6R and inhibits IL-6 mediated angiogenesis and tumor growth.

To accomplish the purposes of the present invention, the oligopeptide selectively binds to IL-6R is identified according to the present invention, which comprises a peptide consisting of 7 amino acid residues that is selected from the group consisting of amino acid sequences listed as SEQ ID NO: 5, SEQ ID NO: 6 and SEQ ID NO: 7. The peptides according to the present invention can specifically compete and inhibit the binding between IL-6 and IL-6R, and interfere the signal transduction mediated through IL-6. IL-6R described above could be membrane type IL-6R in target cells or soluble IL-6R (sIL-6R).

The oligopeptides according to the present invention (SEQ ID NO: 5–7) may be produced by chemical synthesis (the known peptide synthesis technology or instruments), or recombinant DNA technology by incorporating a DNA sequence encoding the desired oligopeptide into phages or vectors and expressing said peptides of the invention in the phages or vectors, which is not limited by these examples.

Because the oligopeptides according to the present invention (SEQ ID NO: 5–7) may be produced by the known peptide synthesis technology or instruments, or using the abovementioned phages or vectors as expression vehicles, they can be applied easier in industry than monoclonal antibodies.

The oligopeptides of the present invention (SEQ ID NO: 5–7) can specifically compete and inhibit with the interaction between IL-6 and IL-6R α chain (abbreviated hereafter as IL-6Rα), and furthermore, they inhibit IL-6-mediated signal transduction. The oligopeptides of the present invention may decrease IL-6-induced Mcl-1 protein up-regulation; moreover, inhibit angiogenesis due to IL-6-induced expression of vascular endothelial growth factor-A (VEGF-A) through up-regulation. In addition, the oligopeptides of the present invention suppress IL-6-induced tumor growth in vivo effectively. Therefore the oligopeptides of the present invention are thus very useful in controlling IL-6-mediated tumor growth.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

(A) Immuno-blotting pictures of each C33A cell lysate in the presence or absence of synthetic peptide S1, synthetic peptide S7 and IL-6 protein. Antibodies used are P-Akt (anti-phospho-Akt), Akt (anti-Akt), P-ERK (anti-phospho-ERK), and ERK (anti-ERK).

(B) Western blot analyses of the antiapoptotic protein Mcl-1 expression in the presence or absence of synthetic peptide S1, synthetic peptide S7 and IL-6 protein. β-actin is used as a negative control.

Bar 1: vector control group (negative control);
Bar 2: IL-6 treated group;
Bar 3: IL-6 plus peptide S1 group;
Bar 4: IL-6 plus peptide S7 group.

Bar 1: vector control group (negative control);
Bar 2: IL-6 treated group;
Bar 3: IL-6 plus peptide S1 group;
Bar 4: IL-6 plus peptide S7 group.

DETAILED DESCRIPTION OF THE PREFERRED EMBODIMENT

The phage display procedures in the present invention are based on screening of 7 amino acid residues in length, which can selectively binds to α chain of IL-6R from a phage peptide library purchased from New England BioLabs (Beverly, Mass., USA).

Screening of the 7-mer peptide phage library of random amino acid sequences containing $2 \times 10^9$ phage clones was carried out with cell culture dishes coated with IL-6Rα (purchased from R&D Systems, Minneapolis, Minn.) in the invention. The abovementioned phage clones were sequentially added to the IL-6Rα coated cell culture dishes for IL-6Rα absorption. Plate-bound phage clones were washed with glycine buffer (pH 2.2) and neutralized with Tris buffer (pH 9.1) to remove the unbound phage clones. After 3 rounds of selection, about 10.3% (31 of 300) of the phage clones analyzed exhibited IL-6α-binding ability (data not shown). These 31 IL-6Rα-binding clones were isolated and analyzed the sequences. Seven DNA sequences were shown to be translated into different peptides and were listed in Table 1 as SEQ ID NO: 1, SEQ ID NO: 2, SEQ ID NO: 3, SEQ ID NO: 4, SEQ ID NO: 5, SEQ ID NO: 6, and SEQ ID NO: 7.

To further confirm the IL-6Rα binding ability of these seven different peptides, individual phage clones inserted with DNA encoding these seven peptides respectively (hereafter labeled as phage clone S1, S2, S3, S4, S5, S6 and S7) were added into cell culture dishes precoated with IL-6Rα ($10^{11}$ pfu/mL). The results revealed that phage S5, phage S6 and phage S7 significantly inhibited the binding of IL-6 to IL-6Ro, while phage S1, phage S2, phage S3 and phage S4 did not.

The binding affinity of phage S7 to different cell lines was determined by the in vitro binding assay. Phage S7 showed higher binding affinity than phage S1 did in all membrane-type IL-6Rα-expressing cell lines. In addition, results of immunofluorescence staining revealed that phage S7 did bind the plasma membrane of C33A cervical cancer cells (data not shown). All the results showed that phage S7 specifically binds to IL-6Rα and blocks the interaction between IL-6 and IL-6R□.

On the other hand, peptides encoded by the inserted DNA in phage S7 (labeled as 'peptide S7' hereafter) were produced by the known peptide synthesis method. The in vitro competition assay of peptide S7 in the present invention revealed that peptide S7 could antagonize the binding of IL-6 to IL-6Rα in different cell lines.

It has been reported that IL-6 acts as an antiapoptotic factor via up-regulation of Mcl-1 protein through the PI3K/Akt and MAPK signaling pathways to reach the goal of antiapoptosis in a variety of human malignancies. The peptide S7 of the present invention inhibited IL-6-induced activation (phosphorylation) of Akt kinase and MAPK kinase. That's to say peptide S7 blocked IL-6-mediated PI3K/Akt and MAPK signaling pathways. Furthermore, peptide S7 inhibited IL-6-induced up-regulation of Mcl-1 protein in order to inhibit the antiapoptotic effects mediated by IL-6. Chemotherapy-induced apoptosis of cancer cells will be enhanced due to loss of IL-6-mediated antiapoptosis and therefore the therapeutic effect of chemotherapy is increased.

In addition, because IL-6 is known to induce the expression of vascular endothelial growth factor-A (VEGF-A) and angiogenesis in cervical cancer, peptide S7 of the present invention is able to block IL-6-induced expressions of VEGF-A protein and mRNA. The examples of cancer cells includes cervical carcinoma, multiple myeloma, Kaposi's sarcoma, prostate cancer and Basal Cell Carcinoma (BCC), but not limited to these. On the other hand, angiogenesis assays were carried out to further confirm that peptide S7 of the present invention greatly attenuated IL-6-induced human umbilical vein endothelial cells (HUVECs) proliferation and capillary-like tubule formation. It is apparent that peptide S7 of the present invention is able to block IL-6-induced angiogenesis.

People who skilled in the art will easily understand through reading the abovementioned description of this specification, the oligopeptides according to the present invention may be produced by incorporating a DNA sequence encoding the desired oligopeptide into expression vectors and expressing the peptides of the present invention via the expression vectors from the known technology. In addition, people who skilled in the art can also learn from this specification that the oligopeptides or the phage clones expressing the peptide of the present invention can be combined with a pharmaceutical acceptable carrier to produce a medical composition to inhibit the IL-6-mediated tumor growth.

In addition, based on the in vivo experiment, the peptide S7 of the present invention further significantly suppresses IL-6-induced tumor growth. Therefore the peptide S7 of the present invention has a fairly good antitumor effect in controlling IL-6-induced tumor growth.

EXAMPLE 1

IL-6Rα Binding Assay of Phage Clones

The binding affinities to IL-6Rα of the 7 independent peptide sequences of the IR-6Rα-binding clones selected from phage display peptide library (Table 1) were confirmed. The phage clones with the inserted DNA encoding these 7 different peptide sequences (phage S1~S7) were added into IL-6Rα coated 96-well cell culture plates ($10^{12}$ pfu/ml) and incubated with IL-6Rα for 1 hour. IL-6 protein (50 ng/ml, 100 μl) was added to the wells and incubated at room temperature for 2 hours. The plates were thoroughly washed with 0.1% BSA (bovine serum albumin)/PBS (phosphate-buffered saline) buffer (pH 8.5). Finally, biotin-conjugated anti-IL-6 monoclonal antibody, horseradish peroxidase (HRP)-conjugated streptavidin and tetramethyl benzidine (TMB) substrate solution were used to perform the known phage Enzyme-Linked Immunosorbent Assay (ELISA) to determine the L-6 protein bound to the cell plates. The absorbance at 450 nm was read with a reference wavelength of 650 nm (A450/650) and got the result shown in FIG. 1.

Figure 1:
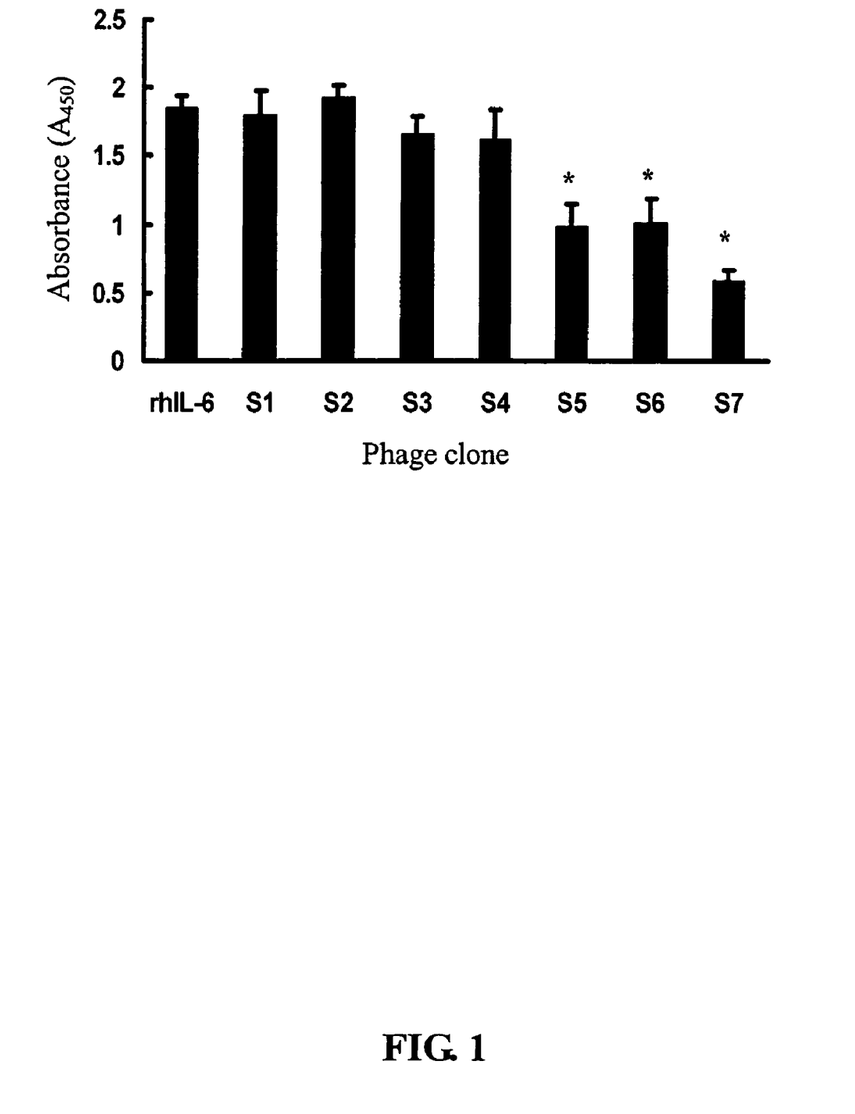
FIG. 1 shows the IL-6R binding ability of each phage clone to compete with IL-6 protein.

The results of FIG. 1 revealed that phage S5, phage S6 and phage S7 significantly inhibited the binding of IL-6 to IL-6Rα, while phage S1, phage S2, phage S3 and phage S4 did not. Phage S7 has the best inhibition effect among them.

EXAMPLE 2

In Vitro Binding Assay of Phage Clones to Different Cell Lines

C33A, HeLa, and Siha (cervical carcinoma) cells, basal cell carcinoma (BCC) cells, and HEK293 fibroblast cells (all were obtained from Invitrogen, Carlsbad, Calif.) were cultivated in DMEM containing 10% fetal bovine serum (FBS). Human umbilical vein endothelial cells (HUVEC) were obtained by digesting human umbilical cords with 0.1% collagenase II, collected and cultivated in M199 medium supplemented with 10% FBS.

Aforementioned cell lines were plated on 96-well plates and cultured to 90% of confluence for phage ELISA analysis. After overnight cultivation, cells were fixed with 0.125%, ice-cold glutaraldehyde at room temperature for 10 min and then washed with PBS. PBS containing 3% BSA were used to block the plates by overnight incubation at 4° C. After blocking, phages S7 ($5 \times 10^{12}$ pfu/ml) were added into the plate and incubated for 2 hours at room temperature. Wells were washed with Tris-buffered saline (TBS, pH 7.5) containing 0.1% Tween 20. Bound phages were detected by ELISA using a horseradish peroxidase (HRP)-conjugated anti-M13 monoclonal antibody (mAb). And the result is shown in FIG. 2.

Figure 2:
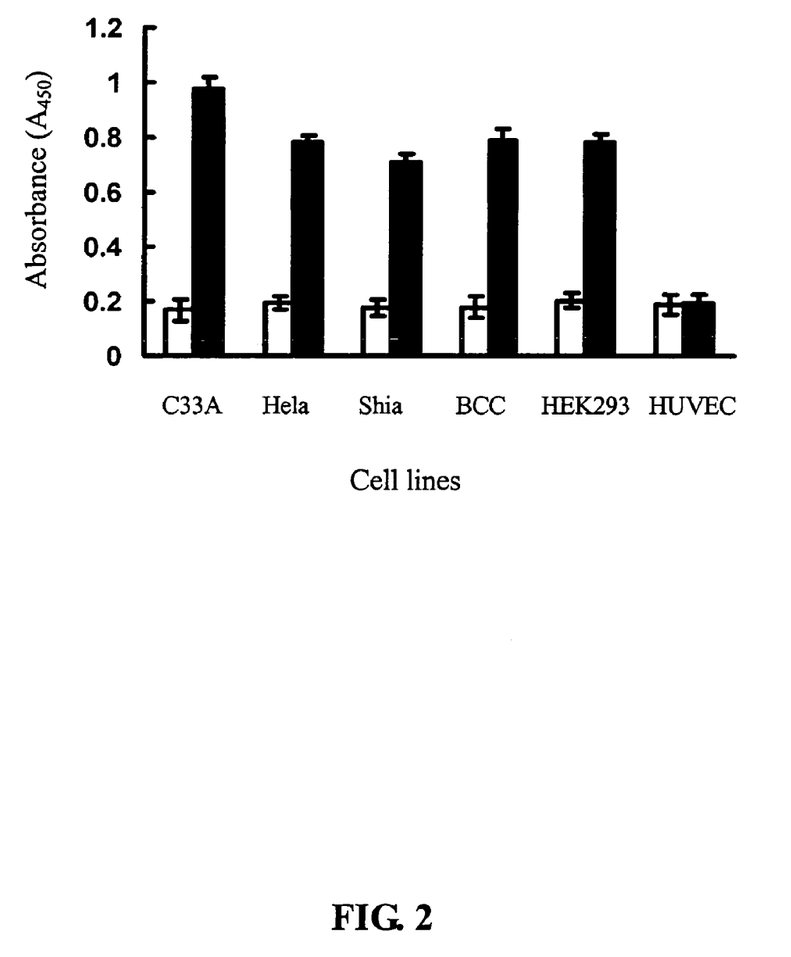
FIG. 2 shows the IL-6R binding abilities of phage clones S1 and S7 to various cell lines; "□" indicated phage clone S1; "■" indicated phage clone S2.

As shown in FIG. 2, phage S7 showed higher binding affinity than phage S1 (negative control) in all membrane-type IL-6Rα-expressing cell lines but not in IL-6Rα negative HUVEC cells.

EXAMPLE 3

In Vitro Competition Assay of Peptide S7

Oligopeptides encoded by the inserted DNA in phages S7 and S1 (labeled as 'peptide S7' (SEQ ID NO: 7) or 'peptide S1' (SEQ ID NO: 1) hereafter) were produced by the known peptide synthesis method. The binding assay described in Example 1 was carried out, but using peptide S7 or peptide S1 (negative control) instead of phage clones, and using cell lines instead of IL-6Rα to perform competition assay and get the result shown in FIG. 3.

Figure 3:
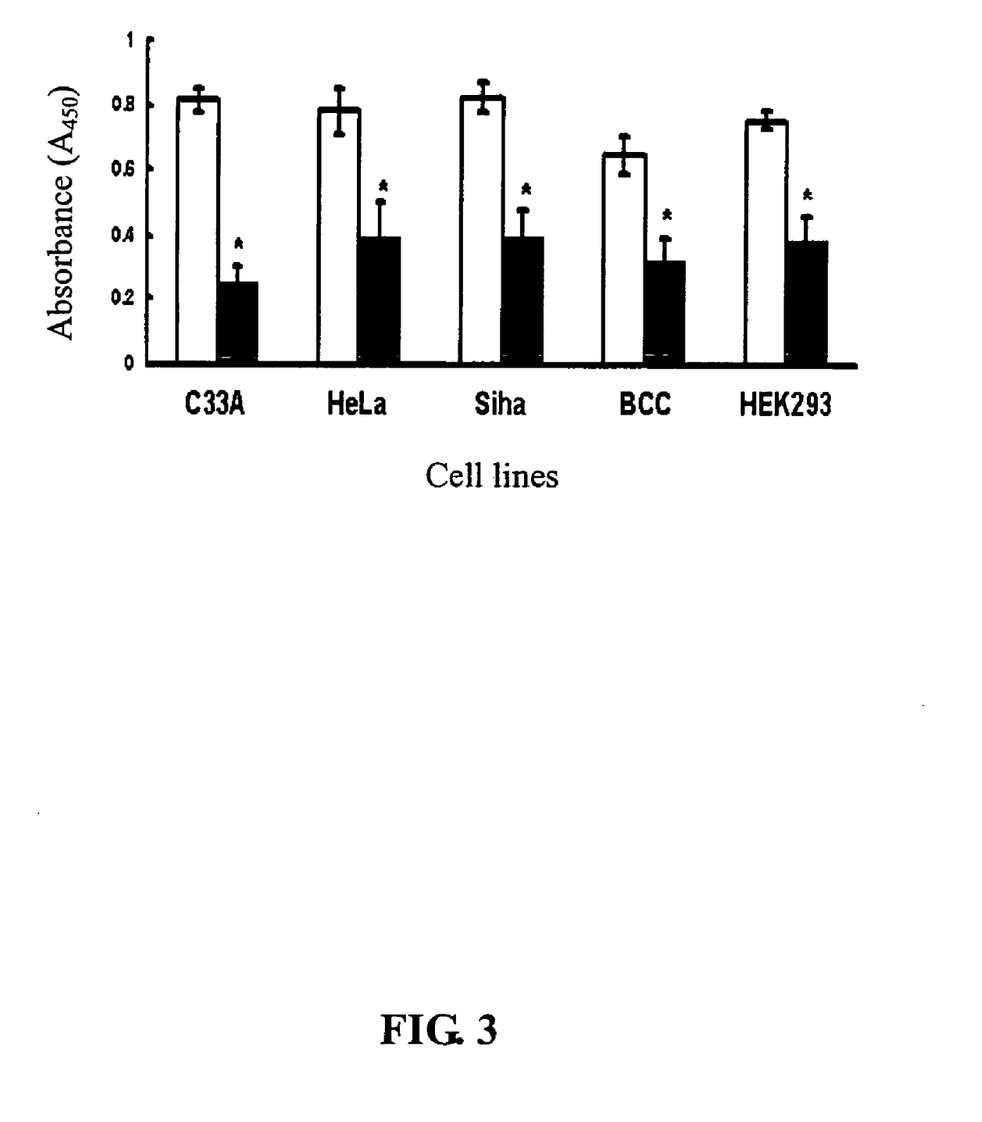
FIG. 3 shows the ability of synthetic peptides S1 and S7 to competitively inhibit the binding of IL-6 protein to IL-6Rα in various cell lines.

FIG. 3 shows that peptide S7 indeed antagonize the binding of IL-6 to IL-6Rα in different cell lines.

EXAMPLE 4

Peptide S7 Inhibits IL-6-Mediated Antiapoptotic Signal Transduction

80% confluent C33A cells were starved for 24 hours and then treated with human IL-6 protein (50 ng/mL) in the presence or absence of S1 peptide (50 μmol/L) or S7 peptide (50 μmol/L). Cell lysates were obtained and subjected to SDS-PAGE separation and Western blot analysis using various antibodies for immunoblotting, such as anti-phospho-ERK1/2, anti-phospho-Akt, anti-ERK1/2, and anti-Akt. The results are shown in FIG. 4A.

Figure 4:
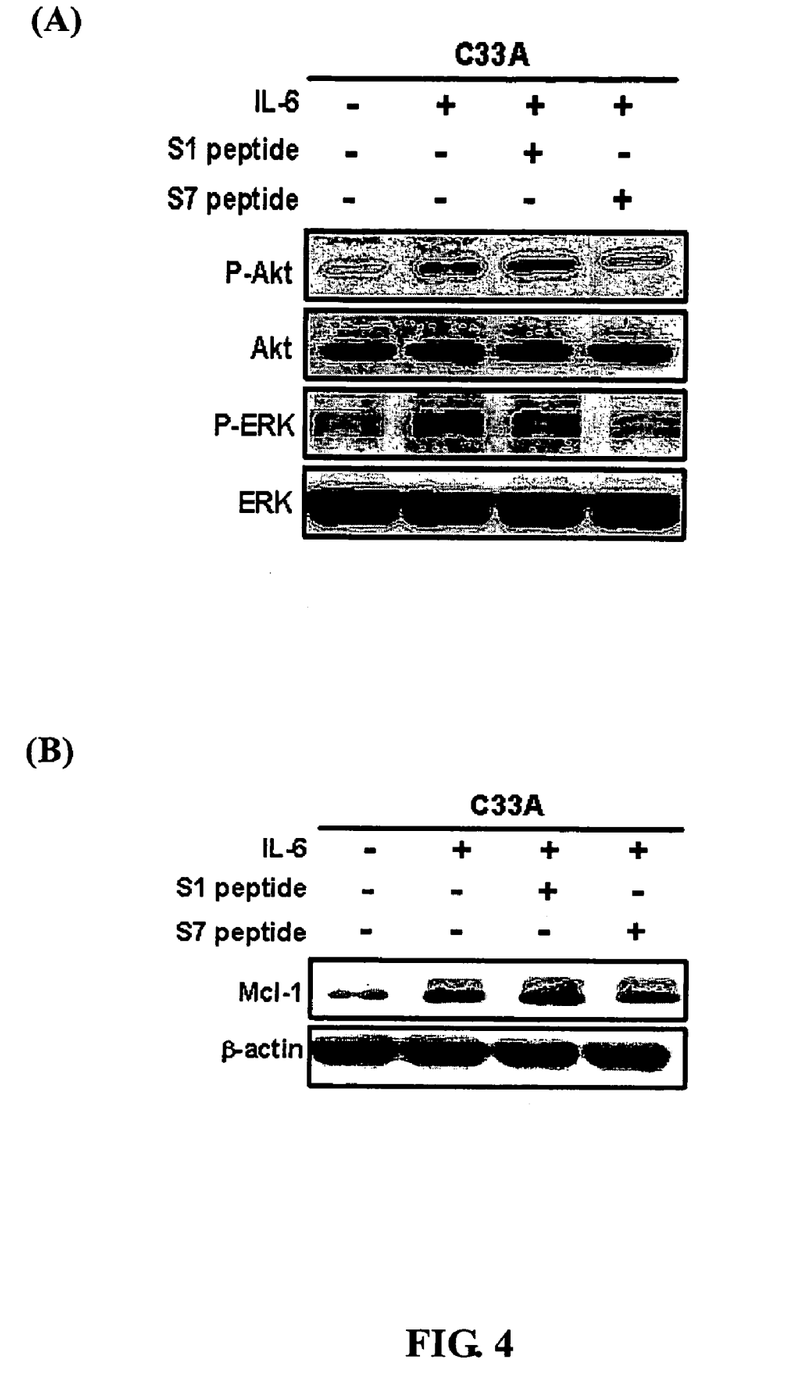
FIG. 4 shows the inhibition of IL-6-mediated antiapoptosis by synthetic peptides analyzed with Western Blotting.

FIG. 4A revealed that the phosphorylated Akt and ERK1/2 MAPK levels were increased in IL-6-treated C33A cervical cancer cells and this activation could be significantly inhibited by peptide S7 treatment but not peptide S1 treatment (negative control). Those results indicate that the Ras/MAPK and PI3-K/Akt signaling pathways could be significantly inhibited by peptide S7 treatment.

Equal amounts of cell lysates (75 μg) were resolved by SDS-PAGE, transferred to polyvinylidene difluoride membranes, and probed with specific anti-Mcl-1 antibodies as described above. β-actin served as the internal loading control to get the result shown in FIG. 4A.

As shown in FIG. 4B, IL-6-induced up-regulation of Mcl-1 protein is also antagonized by peptide S7.

EXAMPLE 5

Peptide S7 Inhibits IL-6-Induced Expressions of VEGF-A and Angiogenesis

C33A cervical cancer cells, RPMI 8226 multiple myeloma cells and basal cell carcinoma (BCC) cells, vectors (negative control) were cultivated respectively in DMEM containing 10% FBS, penicillin (100 units/ml), and streptomycin (100 μg/mL) as well as IL-6 protein. At 90% confluence, culture medium was replaced with serum-free medium. IL-6 containing C33A cells were incubated with S1 or S7 peptide for another 24 hours. Conditioned medium (CM) was collected after centrifugation of cellular debris.

The conditioned medium (CM) was concentrated using an Amicon ultracentrifugation device (Millipore). The concentrations of VEGF-A in culture supernatants were determined with quantitative sandwich ELISA assay according to the manufacturer's instruction. Briefly, cell supernatant (50 μl) was incubated with 50 μl of assay diluents for 2 hours at room temperature in a 96-well tissue culture plate coated with monoclonal antibodies against VEGF-A. After five consecutive washes, a conjugate consisting of polyclonal VEGF-A antibodies and HRP was added. The mixture was incubated for 2 hours at room temperature. Following the subsequent addition of a color reagent, absorbance was read at 450 nm using a Thermo-Max microplate reader (Molecular Devices Co., Menlo Park, Calif.). The results are shown in FIG. 5.

Figure 5:
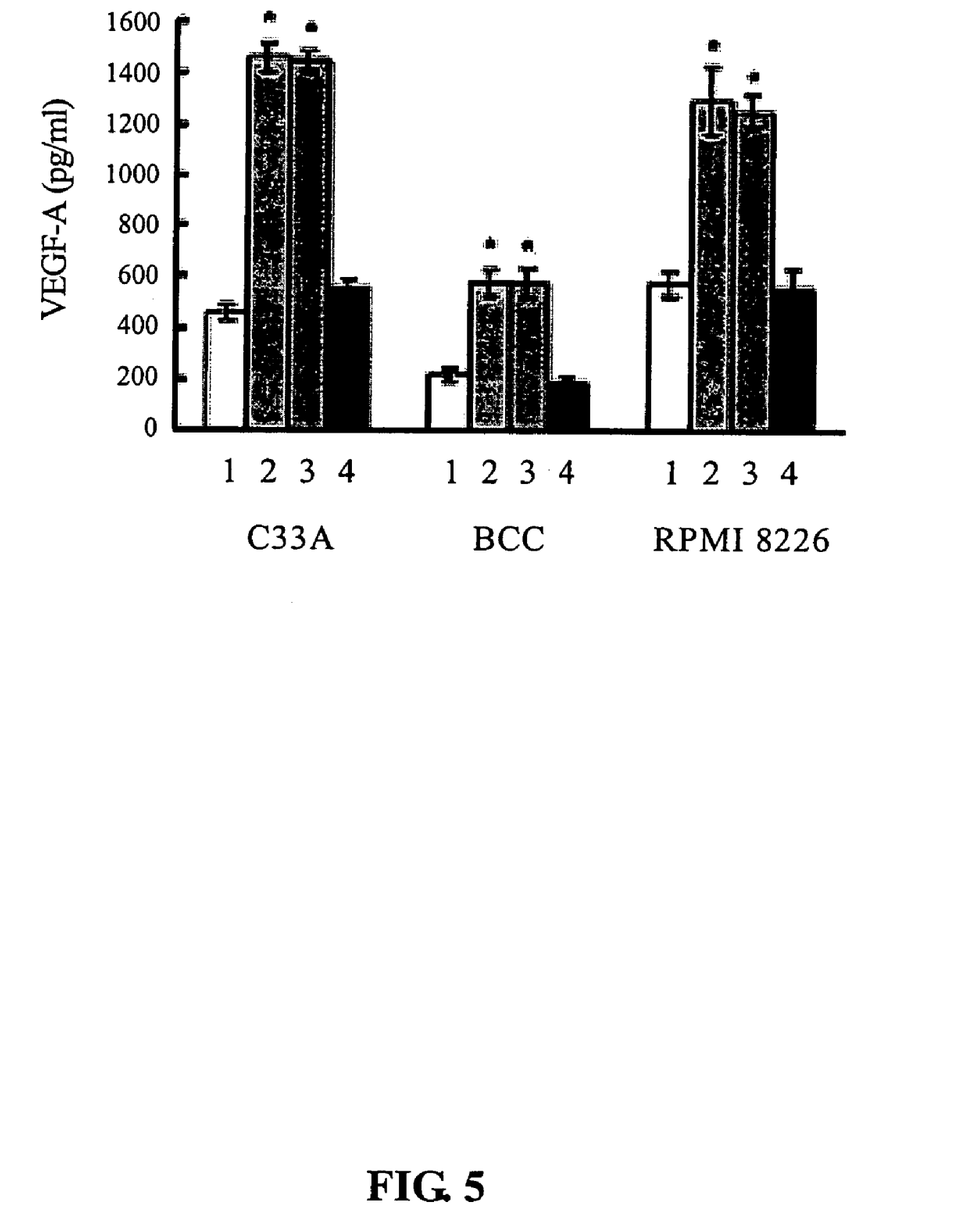
FIG. 5 shows the inhibition of the IL-6-mediated expression of VEGF-A in C33A cells, BCC cells, and RPMI 8226 cells by the synthetic peptide.

As shown in FIG. 5, elevated levels of VEGF-A secretion due to IL-6 stimulation paralleled the increased expression of VEGF-A protein (data not shown), indicating that a mature and functionally active VEGF-A protein was simultaneously generated in IL-6-treated cells. Peptide S7 significantly decreased IL-6-mediated VEGF-A secretion in all three cell lines.

The inhibition of peptide S7 in IL-6-induced angiogenesis activity was analyzed with angiogenesis assays from CM collected as abovementioned, such as proliferation and capillary-like tubules formation by HUVECs in vitro.

HUVECs were plated onto six-well dishes (Falcon, Becton Dickinson) at a concentration of $2.5 \times 10^5$ cells per well in M199 medium supplemented with 10% FBS. One day after seeding, HUVECs were stimulated with CM from cells treated in various ways respectively, where the CM was mixed with M199 medium. Twenty-four hours later, the viable cells were counted using a trypan blue exclusion method.

For the trypan blue exclusion assay, cells were washed with PBS, trypsinized, and then resuspended in 1 ml PBS. Trypan blue-stained cells were then counted using a modified Neubauer hemocytometer under a phase-contrast light microscope. The data was analyzed by statistic methods and is shown in FIG. 6.

Figure 6:
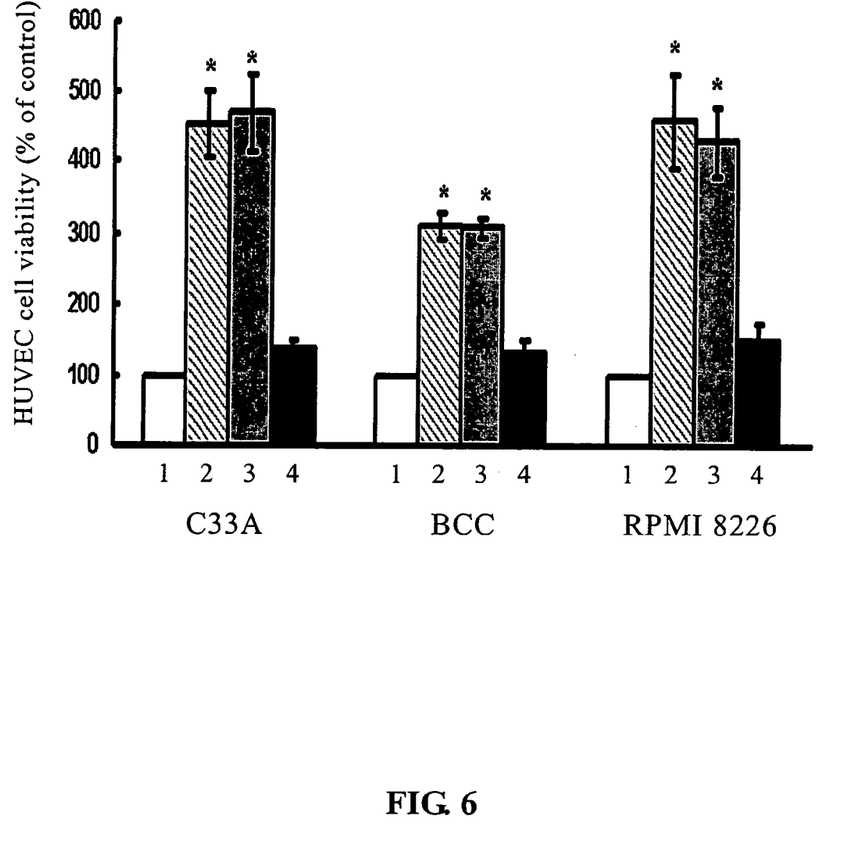
FIG. 6 shows the antagonizing effects on HUVEC cell proliferation in response to the CM from C33A cells, BCC cells, and RPMI 8226 cells stably transfected with human IL-6 cDNA or control vector in the presence or absence of peptide S1 and S7.

As shown in FIG. 6, CM from IL-6-overexpressed cells (IL-6-CM) significantly increased the proliferation of HUVECs, and IL-6-CM induced HUVECs proliferation seemed to be greatly attenuated by peptide S7 but not by peptide S1.

In vitro Assessment using a growth factor-reduced basement membrane Matrigel matrix was carried out to evaluate capillary tube-like formation. The Matrigel was thawed at 4° C. and mixed to homogeneity. The bottom of 96-well cell culture plates were coated with a thin layer of Matrigel (40 µl) and allow the Matrigel to polymerize at 37° C. for 30 minutes. HUVECs were resuspended in M199 medium containing 1% serum to a density of $2.5 \times 10^4$ cells/100 µl, mixed with 100 µl of M199 medium containing 1% serum and 100 µl CM from either C33A/neo or C33A/IL-6 cells treated in various ways, and finally plated onto the Matrigel-coated surface. Six hours later, cells were fixed in 4% paraformaldehyde and stained with 0.1% crystal violet. Three microscopic fields were selected at random and photographed, and the number of tube-like structures per field was determined to get the result shown in FIG. 7.

Figure 7:
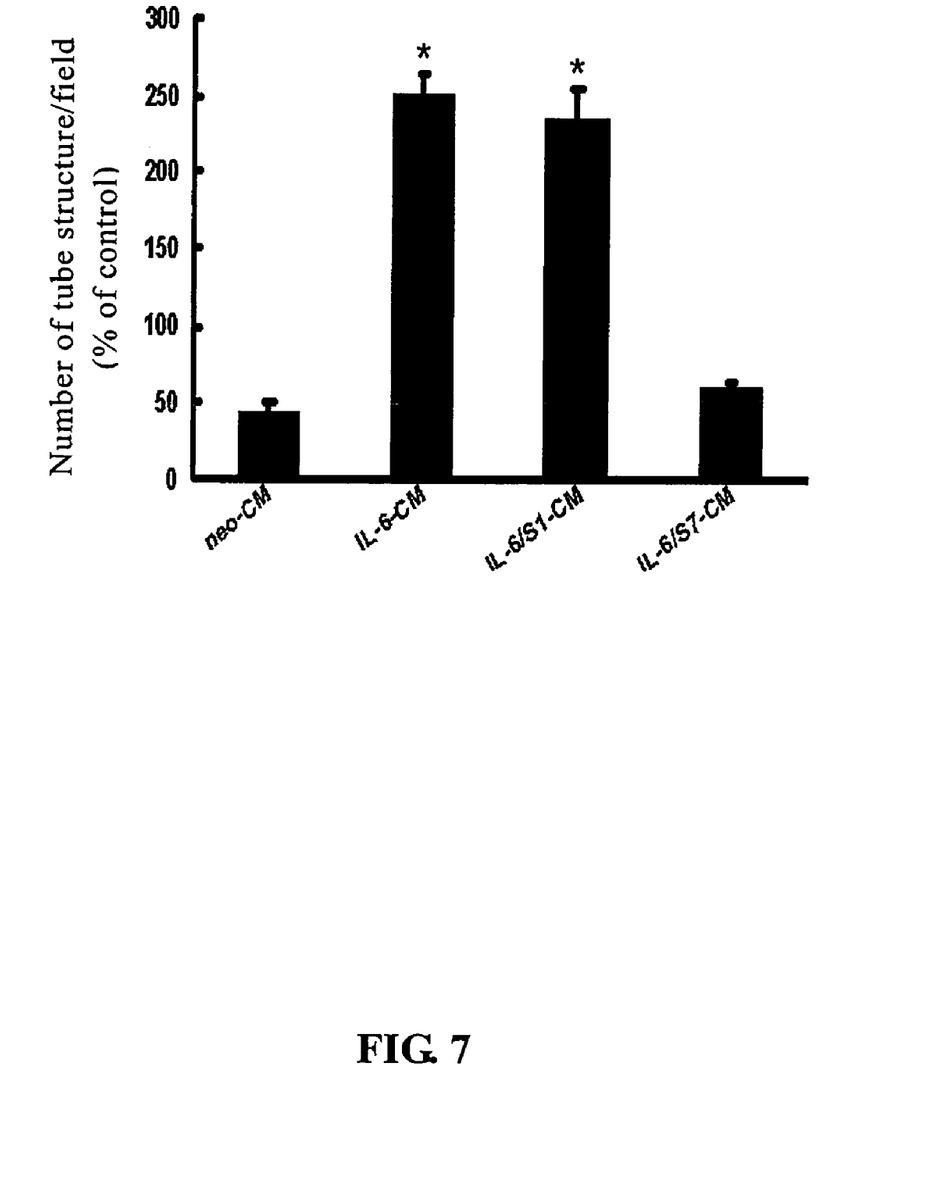
FIG. 7 shows the inhibition of IL-6-induced capillary-like tubules formation treated with peptide S7.

FIG. 7 showed that C33A/IL-6-CM induced tube-like cell cord formation (5.1 fold of the control group), which was almost completely inhibited by peptide S7.

On the other hand, Matrigel plug assay was performed to analyze the inhibiting effect on IL-6-induced angiogenesis of peptide S7. Matrigel (500 µl) containing CM from cells treated in various ways was iv-injected into 4- to 8-week-old female BALB/c nude mice at sites lateral to the abdominal midline. Aforementioned CM was obtained either from vector control cells or from IL-6 overexpressed C33A cells in the presence or absence of peptide S7. The Matrigel plugs were recovered after 7 days of implementation, dissolved in PBS, and incubated at 4° C. overnight. Hemoglobin levels were determined using Drabkin's solution (Sigma Chemical) according to the manufacturer's instructions to get the result shown in FIG. 8.

Figure 8:
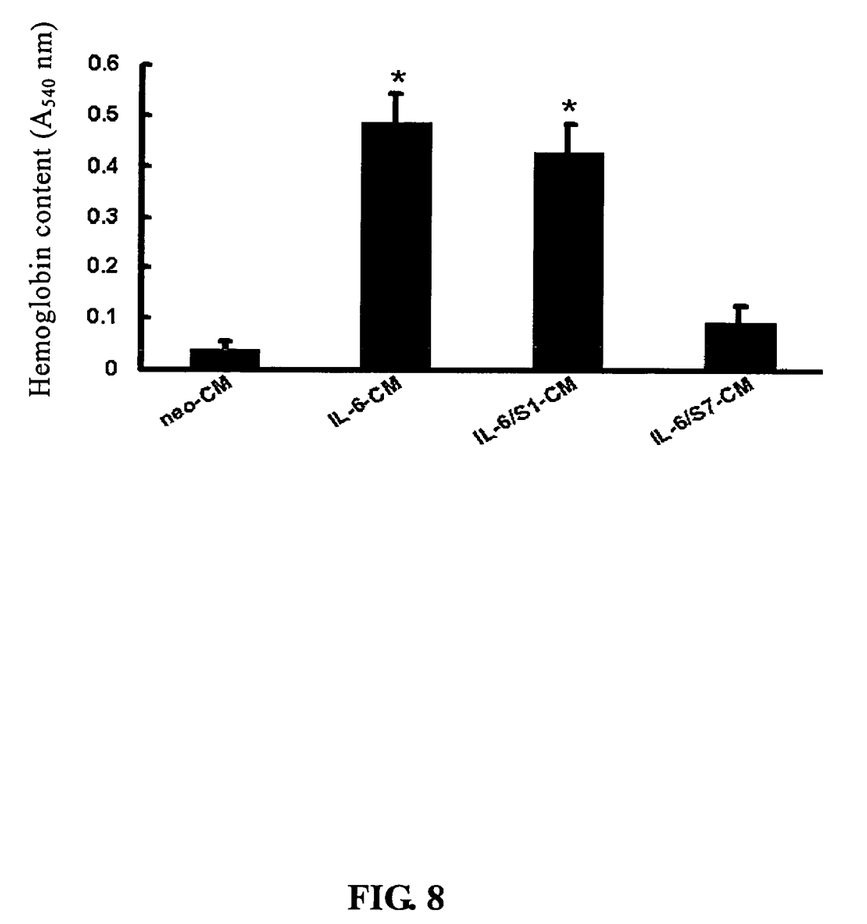
FIG. 8 shows the inhibition of IL-6-induced angiogenesis treated with peptide S7.

Result of FIG. 8 clearly showed that hemoglobin level was significantly elevated in plugs containing C33A/IL-6-CM than in plugs containing C33A/neo-CM, and hemoglobin induction was almost completely inhibited by peptide S7.

Therefore, all the results from the above angiogenesis experiments showed that peptide S7 of the invention effectively blocked IL-6-induced expression of VEGF-A and the angiogenesis.

EXAMPLE 6

Analysis of Tumor Growth Inhibition

Six- to 8-week-old female severe combined immunodeficient (SCID) mice were iv-injected with $1 \times 10^6$ C33A/neo or C33A/IL-6 cells. Beginning 3 days later, S1 or S7 peptide (50 mg/kg, dissolved in PBS) was injected i.p. every 2 days. Tumor development was followed in measurements of length (L) and width (W). Tumor volume was calculated with the formula of $L^2W/2$ to get the result shown in FIG. 9.

Figure 9:
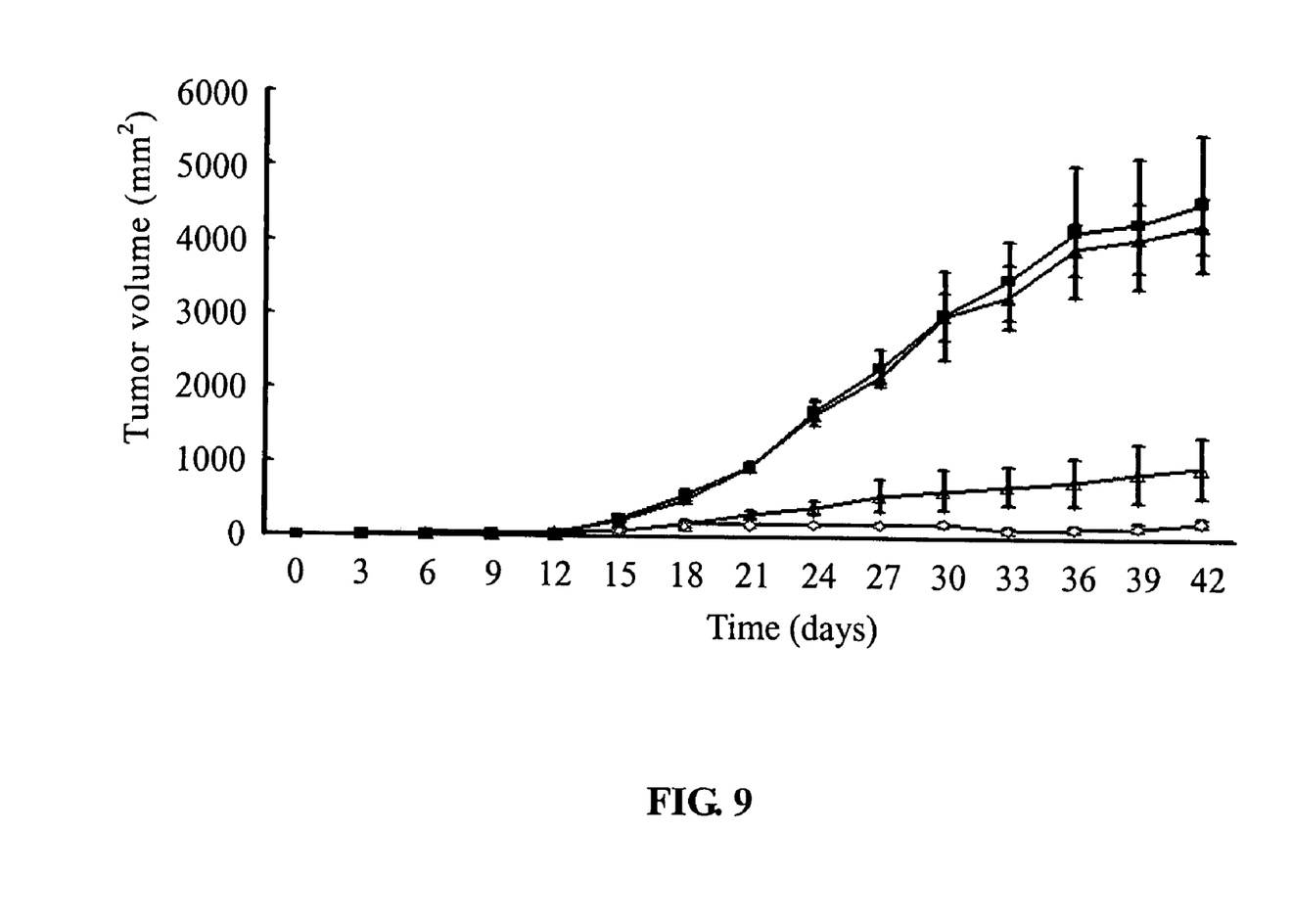
FIG. 9 shows the inhibition of IL-6-induced tumor growth in vivo treated with peptide S7.

FIG. 9 showed that showed that administration of peptide S7 significantly reduced IL-6-induced tumor growth, and peptide S7 inhibited tumor growth by 76% at the end of the experiment.

These results from the above experiments showed an excellent antitumor effect of peptide S7 in inhibition of IL-6-induced tumor growth.

TABLE 1

Sequences of the peptides selected by binding to IL-6R

| Phage clone | Encoded Insert | Sequence Number |
| --- | --- | --- |
| S1 | Leu-Ser-Leu-Met-Pro-Arg-Leu | SEQ ID NO:1 |
| S2 | Asn-Pro-Met-Met-Arg-Pro-Leu | SEQ ID NO:2 |
| S3 | Gln-Met-Arg-Thr-Thr-Ile-Arg | SEQ ID NO:3 |
| S4 | Arg-Leu-Met-Met-Leu-Gln-Gln | SEQ ID NO:4 |
| S5 | Met-Leu-Leu-Gln-Asn-Arg-Gln | SEQ ID NO:5 |
| S6 | Thr-Leu-Gln-Ala-Ser-Ile-Leu | SEQ ID NO:6 |
| S7 | Leu-Ser-Leu-Ile-Thr-Arg-Leu | SEQ ID NO:7 |

What is claimed is:

1. An oligopeptide antagonist of interleukin-6, wherein the oligopeptide antagonist specifically binds interleukin-6 receptor and competes for the binding of the interleukin-6 to the interleukin-6 receptor, wherein the oligopeptide antagonist comprises an amino acid sequence of SEQ ID NO: 5.

2. An oligopeptide antagonist of interleukin-6, wherein the oligopeptide antagonist specifically binds interleukin-6 receptor and competes for the binding of the interleukin-6 to the interleukin-6 receptor, wherein the oligopeptide antagonist comprises an amino acid sequence of SEQ ID NO: 5 and wherein the interleukin-6 receptor is soluble interleukin-6 receptor.

3. An oligopeptide antagonist of interleukin-6, wherein the oligopeptide antagonist specifically binds interleukin-6 receptor and competes for the binding of the interleukin-6 to the interleukin-6 receptor, wherein the oligopeptide antagonist comprises an amino acid sequence of SEQ ID NO: 5 and wherein the interleukin-6 receptor is membrane type interleukin-6 receptor in target cells.

4. The oligopeptide antagonist of interleukin-6 as claimed in claim 3, wherein the target cells are cancer cells.

5. The oligopeptide antagonist of interleukin-6 as claimed in claim 4, wherein the cancer cells are selected from the group consisting of multiple myeloma, Kaposi's sarcoma, prostate cancer, basal cell carcinoma and cervical cancer.

6. An oligopeptide antagonist of interleukin-6, wherein the oligopeptide antagonist specifically binds interleukin-6 receptor and competes for the binding of the interleukin-6 to the interleukin-6 receptor, wherein the oligopeptide antagonist comprises an amino acid sequence of SEQ ID NO: 5 and wherein the oligopeptide specifically binds to a chain protein of the interleukin-6 receptor.

7. A medical composition, which comprises an effective dosage of the oligopeptide antagonist as claimed in claim 1, and a pharmaceutically acceptable carrier.

8. An oligopeptide antagonist of interleukin-6, wherein the oligopeptide antagonist specifically binds interleukin-6 receptor and competes for the binding of the interleukin-6 to the interleukin-6 receptor, wherein the oligopeptide antagonist consists of an amino acid sequence that is SEQ ID NO: 6 or SEQ ID NO: 7.

9. A medical composition, which comprises an effective dosage of the oligopeptide antagonist as claimed in claim 8, and a pharmaceutically acceptable carrier.

* * * * *